(12) United States Patent
Chwae et al.

(10) Patent No.: US 9,181,170 B2
(45) Date of Patent: Nov. 10, 2015

(54) METHOD FOR PREPARING UNSATURATED CARBOXYLIC ACID

(71) Applicant: Samsung Electronics Co. Ltd., Suwon-si, Gyeonggi-do (KR)

(72) Inventors: Jun Chwae, Seoul (KR); Nam Soo Park, Suwon-si (KR); Moo Ho Lee, Suwon-si (KR); Jong Won Kim, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/098,154

(22) Filed: Dec. 5, 2013

(65) Prior Publication Data

US 2014/0171681 A1    Jun. 19, 2014

(30) Foreign Application Priority Data

Dec. 7, 2012 (KR) .......... 10-2012-0142180

(51) Int. Cl.
*C07C 51/347* (2006.01)
*C07C 51/377* (2006.01)

(52) U.S. Cl.
CPC ............. *C07C 51/347* (2013.01); *C07C 51/377* (2013.01)

(58) Field of Classification Search
CPC combination set(s) only.
See application file for complete search history.

(56) References Cited

U.S. PATENT DOCUMENTS

| | | | |
|---|---|---|---|
| 2,469,701 A | 5/1949 | Redmon | |
| 6,942,803 B2 * | 9/2005 | Cockrem et al. | ............. 210/639 |
| 7,629,162 B2 | 12/2009 | Zhou et al. | |
| 7,638,316 B2 | 12/2009 | Gokarn et al. | |
| 8,048,624 B1 | 11/2011 | Lynch | |
| 8,198,481 B2 * | 6/2012 | Kuppinger et al. | ........... 562/600 |
| 2005/0221457 A1 | 10/2005 | Tsobanakis et al. | |
| 2005/0222458 A1 | 10/2005 | Craciun et al. | |
| 2013/0157328 A1 * | 6/2013 | Ozmeral et al. | ............. 435/135 |

FOREIGN PATENT DOCUMENTS

WO    WO 2013/095009 A1    6/2013

* cited by examiner

*Primary Examiner* — Karl J Puttlitz
(74) *Attorney, Agent, or Firm* — Leydig, Voit & Mayer, Ltd.

(57) ABSTRACT

A method for preparing an unsaturated carboxylic acid comprising (a) preparing an aqueous solution comprising an ammonium salt of hydroxycarboxylic acid and a salt of inorganic acid; (b) contacting the aqueous solution with a cation exchange resin to prepare a conversion aqueous solution comprising a hydroxycarboxylic acid and an inorganic acid; and (c) dehydrating the hydroxycarboxylic acid using the inorganic acid as a catalyst is provided.

10 Claims, No Drawings

METHOD FOR PREPARING UNSATURATED CARBOXYLIC ACID

CROSS-REFERENCE TO RELATED APPLICATIONS

The present application claims the benefit of Korean Patent Application No. 10-2012-0142180, filed on Dec. 7, 2012, in the Korean Intellectual Property Office, the entire disclosure of which is incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,091 Byte ASCII (Text) file named "715456_ST25.TXT," created on Dec. 4, 2013.

BACKGROUND OF THE INVENTION

1. Field of the Invention

The present invention relates to a method for preparing an unsaturated carboxylic acid using an ammonium salt of hydroxycarboxylic acid.

2. Description of the Related Art

Acrylic acid is an unsaturated carboxylic acid, and polyacrylic acid is widely used for preparing water-absorbing resins. Currently, such acrylic acid is prepared via a two-step oxidation process of propylene in the presence of an oxide catalyst. Propylene, as the raw material of acrylic acid, can be obtained from petroleum, but the price of propylene is rising due to increased demand for petroleum.

In order to prepare acrylic acid independent of petroleum, dehydration of biomass-derived lactic acid or 3-hydroxypropionic acid to acrylic acid has been reported. In addition, conversion of lactate or 3-hydroxypropionate produced by fermentation of biomass into acrylic acid has been studied.

U.S. Pat. No. 2,469,701 discloses a method for preparing acrylic acid by supplying 3-hydroxypropionic acid (3HP) in a reactor containing a dehydration catalyst under heating and reduced-pressure conditions. However, there is no mention of conversion of 3-hydroxypropionate generated during fermentation into acrylic acid.

U.S. Patent Publication No. 2005-0222458 discloses a method for preparing acrylic acid by heating 3-hydroxypropionic acid or its derivatives obtained from microbial or plant cells. Specifically, acrylic acid is prepared by vapor-phase dehydration of 3-hydroxypropionic acid in the presence of a heterogeneous catalyst, such as silica, alumina, or titania. When the heterogeneous catalyst is used, acrylic acid can be obtained in a high yield, but there is the problem of catalyst contamination due to organic impurities, which reduces catalyst performance.

U.S. Patent Publication No. 2005-0221457 discloses a method for preparing a salt (or ester) of acrylic acid by heating the salt (or ester) of 3-hydroxypropionic acid. However, this method concerns only the conversion of sodium and calcium salts of 3-hydroxypropionic acid at elevated pressure, and the yield of acrylic acid by dehydration is poor (41.8%, 48.7%).

U.S. Pat. No. 8,198,481 discloses a method for preparing acrylic acid by a two-step reaction of 3-hydroxypropionic acid and phosphoric acid. However, the two-step reaction adds cost to the overall process by requiring additional unit operations and equipment, as well as by generating additional wastes.

Therefore, there remains a desire for a method for preparing an unsaturated carboxylic acid in a simple and economic manner and in a high yield.

SUMMARY OF THE INVENTION

An embodiment of the present invention provides a method for preparing an unsaturated carboxylic acid comprising (a) preparing an aqueous solution comprising an ammonium salt of hydroxycarboxylic acid and a salt of inorganic acid; (b) contacting the aqueous solution with a cation exchange resin to prepare a conversion aqueous solution comprising a hydroxycarboxylic acid and an inorganic acid; and (c) dehydrating the hydroxycarboxylic acid using the inorganic acid as a catalyst.

In this regard, the salt of inorganic acid of step (a) may be one or more selected from the group consisting of phosphate and sulfate.

Further, the aqueous solution including the ammonium salt of hydroxycarboxylic acid and the salt of inorganic acid of step (a) may be derived from a fermentation broth of microorganisms.

Further, the cation exchange resin of step (b) may have an acid dissociation constant (pKa) which is 0.5 less than that of the inorganic acid of step (b).

Further, step (b) may further include the step of washing the ammonium ion-adsorbed cation exchange resin with an acid to regenerate ammonia.

Meanwhile, the present invention provides an unsaturated carboxylic acid prepared by the above method and an ester prepared by esterification of the unsaturated carboxylic acid.

DETAILED DESCRIPTION OF THE PREFERRED EMBODIMENTS

1. Preparation Method of Unsaturated Carboxylic Acid

An embodiment of the present invention provides a method for preparing an unsaturated carboxylic acid without additional injection of a catalyst using an ammonium salt of hydroxycarboxylic acid that is generated during the production process of hydroxycarboxylic acid from a carbon source by microbial fermentation. A detailed description of the preparation method is as follows.

A) Preparation of Aqueous Solution

First, an aqueous solution including an ammonium salt of hydroxycarboxylic acid and a salt of inorganic acid is prepared. The aqueous solution is not particularly limited, as long as it includes the ammonium salt of hydroxycarboxylic acid and the salt of inorganic acid. Preferably, the aqueous solution is derived from a fermentation broth that is obtained by fermentation of a hydroxycarboxylic acid-producing microorganism.

When hydroxycarboxylic acid is prepared by microbial fermentation of a carbon source such as glucose or glycerol, ammonia or an amine-based compound is injected during fermentation in order to neutralize the reduced pH of a fermentation broth due to the generated hydroxycarboxylic acid. Consequently, a salt of hydroxycarboxylic acid and ammonia or amine-based compound is formed and thus a large amount of the ammonium salt of hydroxycarboxylic acid is present in the fermentation broth. The amine-based compound may include primary, secondary, and tertiary amines, and specific examples thereof may include trimethylamine, triethylamine, dibutylamine, diamine or the like.

For cell growth and protein expression during fermentation, an inorganic acid such as phosphorus (P) or sulfur (S) is added in the form of salt as a medium component, and, thus, a salt of the inorganic acid is also present in the fermentation broth. In particular, phosphate is added as a buffer for preventing the pH reduction of the fermentation broth when the pH drops due to the microorganism's metabolism.

When the aqueous solution derived from the fermentation broth including the ammonium salt of hydroxycarboxylic acid and the salt of inorganic acid generated by microbial fermentation is used, an inorganic acid that functions as a catalyst in the preparation of unsaturated carboxylic acid can be obtained from the salt of inorganic acid.

The salt of inorganic acid included in the aqueous solution is not particularly limited, but preferably is one or more selected from the group consisting of phosphate and sulfate. That is, phosphate or sulfate may be singly included in the aqueous solution, or both of phosphate and sulfate may be included. In this regard, the salt of inorganic acid is provided in the form of an ammonium, potassium, sodium, magnesium, or iron salt. Herein, non-limiting examples of phosphate and sulfate may include $(NH_4)_2HPO_4$, $KH_2PO_4$, $NaH_2PO_4$, $Na_2HPO_4$, $KH_2PO_4$, $K_2HPO_4$, $MgSO_4$, $FeSO_4$, or the like.

The ammonium salt of hydroxycarboxylic acid included in the aqueous solution is not particularly limited, as long as it is a salt in which ammonia or amine-based compound is bound to hydroxycarboxylic acid. Herein, hydroxycarboxylic acid bound to ammonia or amine-based compound is not particularly limited, but preferably one or more selected from the group consisting of lactic acid, citric acid, malic acid, tartaric acid, glycolic acid, 3-hydroxypropionic acid, 3-hydroxy-2-methylpropionic acid, 3-hydroxybutyric acid, 3-hydroxyvaleric acid, 3-hydroxyhexanoic acid, 3-hydroxyheptanoic acid, 3-hydroxyoctanoic acid, 3-hydroxy-2-methylbutyric acid, 3-hydroxy-2-methylpentanoic acid, 3-hydroxy-3-methylbutyric acid, 2,3-dimethyl-3-hydroxybutyric acid and 3-hydroxy-3-phenylpropionic acid, and more preferably, lactic acid or 3-hydroxypropionic acid.

The microorganism used for the preparation of the aqueous solution of the present invention is not particularly limited, as long as it produces hydroxycarboxylic acid by a natural or recombinant method, and non-limiting examples thereof may include *Escherichia coli, Bacillus coagulans, Lactobacillus delbruckii, L. bulgaricus, L. thermophilus, L. leichmanni, L. casei, L. fermentii, Streptococcus thermophilus, S. lactis, S. faecalils, Pediococcus* sp, *Leuconostoc* sp, *Bifidobacterium* sp, *Rhizopus oryzae* or the like (see, e.g., U.S. Pat. Nos. 7,629,162, 7,638,316, and 8,048,624, WO2013/095009, etc.).

Hydroxycarboxylic acid can be prepared from the microorganism by batch, fed-batch or continuous fermentation.

As the aqueous solution of the present invention, the fermentation broth may be used as it is, or the fermentation broth may be pre-treated by a method of centrifugation, membrane filtration, activated carbon filtration, liquid-liquid extraction, electrodialysis or the like, and an aqueous component of the fermentation broth comprising an ammonium salt of a hydroxycarboxylic acid and a salt of an inorganic acid can be used as the aqueous solution.

The content of the ammonium salt of hydroxycarboxylic acid in the aqueous solution of the present invention is not particularly limited, but the content is preferably 0.1 to 50 w/v % (e.g., 0.5 w/v %, 1 w/v %, 5 w/v %, 10 w/v %, 15 w/v %, 20 w/v %, 25 w/v %, 30 w/v %, 35 w/v %, 40 w/v % or 45 w/v %), and more preferably 0.5 to 30 w/v %, based on 100 w/v % of the aqueous solution, considering the exchange efficiency of the cation exchange resin.

B) Formation of Conversion Aqueous Solution

Next, the ammonium ion bound to the ammonium salt of hydroxycarboxylic acid and the metal ion bound to the salt of the inorganic acid are adsorbed onto the cation exchange resin by contacting the prepared aqueous solution with the cation exchange resin, so as to form a conversion aqueous solution including hydroxycarboxylic acid and inorganic acid. In other words, the ammonium salt of hydroxycarboxylic acid is separated into a hydroxycarboxylic acid and an ammonium ion and the inorganic acid is separated into an inorganic acid and a metal ion using the cation exchange resin exchanging its own cations with cations in the aqueous solution.

Since the inorganic acid is more acidic than hydroxycarboxylic acid, an acid dissociation constant ($pK_a$) of the inorganic acid is lower than that of hydroxycarboxylic acid. Therefore, in order to separate the ammonium salt of hydroxycarboxylic acid and the salt of inorganic acid into acids and ions by contacting the salts with the cation exchange resin, the cation exchange resin preferably has a lower acid dissociation constant ($pK_a$), and more preferably has an acid dissociation constant ($pK_a$) being 0.5 less than that of the inorganic acid (e.g., less than the lowest pKa of a polyprotic acid).

In detail, if the salt of inorganic acid is phosphate and/or sulfate, a conversion aqueous solution including hydroxycarboxylic acid and phosphoric acid and/or sulfuric acid is formed by contacting the aqueous solution including phosphate and/or sulfate with the cation exchange resin. The acid dissociation constant ($pK_a$) of the cation exchange resin is 0.5 less than that of sulfuric acid which is more acidic than phosphoric acid. That is, if a plurality of inorganic acids is used, the cation exchange resin having an acid dissociation constant ($pK_a$) that is 0.5 less than that of the most acidic inorganic acid is preferably used. More preferably, the cation exchange resin has an acid dissociation constant ($pK_a$) that is 1.0 less than that of the inorganic acid.

As used herein, the acid dissociation constant means an equilibrium constant that refers to the ionization of an acid, and represented by $K_a$ or $pK_a$ ($-\log K_a$). In the present invention, the acid dissociation constant is defined as $pK_a$, which means that the lower $pK_a$ is a stronger acid. For reference, the maximum $pK_a$ of phosphoric acid is 2.15, and the maximum $pK_a$ of sulfuric acid is −3.

The cation exchange resin is not particularly limited, as long as the resin has an acid dissociation constant ($pK_a$) that is 0.5 less than that of the inorganic acid. Non-limiting examples thereof may include a TRILITE resin (manufactured by Samyang Co. (Jongno-gu, Seoul, Korea)), a LEWATIT® resin (manufactured by LANXESS Korea Ltd. (Dongjak-gu, Seoul, Korea)), a DOWEX™ resin (manufactured by Dow Chemical (Kangnam-ku, Seoul, Korea)) or the like.

The content (concentration) of hydroxycarboxylic acid in the conversion aqueous solution formed through the above process is not particularly limited, but it is preferably 5 to 95 wt % (e.g., 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, or 90 wt %), and more preferably 10 to 90 wt %, based on 100 wt % of the conversion aqueous solution for efficient dehydration. Further, the content (concentration) of inorganic acid in the conversion aqueous solution is preferably 0.1 to 5 wt %, based on 100 wt % of the conversion aqueous solution.

When the ammonium salt of hydroxycarboxylic acid and the salt of inorganic acid are contacted with the cation exchange resin, ammonium ions and metal ions are adsorbed onto the cation exchange resin. The present invention may further include the step of regenerating ammonia by washing the ammonium ion-adsorbed cation exchange resin with an acid.

In other words, ammonia is regenerated from the ammonium ion-adsorbed cation exchange resin using a washing acid having an acid dissociation constant ($pK_a$) that is at least 0.5 less than that of the acidic ion exchange resin. Specifically, the washing acid such as HCl is passed through the cation exchange resin to exchange the ammonium ions and metal ions adsorbed onto the cation exchange resin with $H^+$ ions of the washing acid, thereby regenerating the cation exchange resin. At this time, HCl passed through the cation exchange resin is converted into the aqueous solution in which ammonium ions and metal ions bind to $Cl^-$ and they exist in the form of a salt. Ammonia and a strong acid can be recovered by heating this aqueous solution.

C) Dehydration

When the conversion aqueous solution including hydroxycarboxylic acid and inorganic acid is formed through the above process, dehydration of hydroxycarboxylic acid is performed using the inorganic acid included in the conversion aqueous solution as a catalyst so as to prepare an unsaturated carboxylic acid. That is, the catalyst needed for dehydration is obtained from the salt of inorganic acid that is included in the aqueous solution derived from the fermentation broth.

When the salt of inorganic acid included in the aqueous solution is converted into an acid and the converted inorganic acid is used as a catalyst, it is not necessary to further add a catalyst for dehydration. Therefore, the unsaturated carboxylic acid can be prepared in a simple and economic manner. In order to facilitate the dehydration, an additional dehydration catalyst may be added during dehydration. In this regard, the additional catalyst may include an acid catalyst such as sulfuric acid, phosphoric acid or the like, or a heterogeneous catalyst such as gamma alumina, $TiO_2$, zeolite, $CuSO_4$-silica gel.

If the salt of inorganic acid is phosphate and/or sulfate, the phosphate and/or sulfate are (is) converted into phosphoric acid and/or sulfuric acid through the conversion process, and the converted phosphoric acid and/or sulfuric acid function(s) as a catalyst.

The dehydration may be performed by adding a solvent, preferably a water-miscible solvent, to the conversion aqueous solution including hydroxycarboxylic acid and inorganic acid (specifically, phosphoric acid and/or sulfuric acid), injecting the mixture into a reactor, and heating the mixture. The solvent, preferably the water-miscible solvent added to the conversion aqueous solution is not particularly limited, but water is preferably used. Further, the reactor-heating temperature may be 100 to 350° C. (e.g., 110° C., 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., 300° C., 310° C., 320° C., 330° C., or 340° C.), preferably 170 to 220° C., and more preferably 185 to 205° C. Further, the pressure is preferably atmospheric pressure. The resulting unsaturated carboxylic acid has a lower boiling point than hydroxycarboxylic acid, and thus can be recovered during dehydration.

When the conventional heterogeneous catalyst is used to perform dehydration, the inorganic acid or organic substance present in the aqueous solution contaminates the surface of the catalyst so as to deteriorate the catalytic performance and to reduce lifetime thereof. However, these problems can be solved by using a homogeneous catalyst such as inorganic acid (specifically, phosphoric acid and/or sulfuric acid), as in the present invention.

2. Unsaturated Carboxylic Acid and Ester Using the Same

The present invention provides an unsaturated carboxylic acid prepared by the preparation method described above. The unsaturated carboxylic acid prepared by the above method is not particularly limited, but it is preferably selected from the group consisting of acrylic acid, methacrylic acid and crotonic acid, and more preferably, acrylic acid.

When the unsaturated carboxylic acid prepared by the above preparation method is acrylic acid, the resulting acrylic acid can be separated by a separation method known in the art. Non-limiting examples of the separation method may include an azeotropic distillation, absorption, or extraction process by adding toluene or xylene to the final product including acrylic acid, water or the like. Further, the method for purifying the separated acrylic acid is not particularly limited, as long as a purification equipment and method known in the art are used.

The present invention provides an ester that is prepared by esterification of alcohol and an unsaturated carboxylic acid prepared by the above method. In this regard, the esterification method of unsaturated carboxylic acid is not particularly limited, as long as it is known in the art. Further, alcohol to be used may be a monovalent alcohol or a polyvalent alcohol, and the alcohol may have 1 to 8 carbon atoms.

The catalyst for esterification may be an inorganic acid, an organic acid, a solid acid or the like, but the organic acid or solid acid is preferred in terms of separation of the acid catalyst. Specifically, the reaction catalyst may include one or more inorganic acids selected from sulfuric acid, phosphoric acid, and nitric acid; one or more organic acids selected from methanesulfonic acid and p-toluene sulfonic acid (pTSA); one or more solid acids selected from zeolite and polymer resin, or the like. Meanwhile, the esterification may be performed in a reactor continuously operated, and the reaction temperature is room temperature to 300° C. (e.g., 20° C., 25° C., 30° C., 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C., 260° C., 270° C., 280° C., or 290° C.), and preferably 60 to 200° C.

The preparation method of unsaturated carboxylic acid of the present invention also may be used in conversion of unsaturated carboxylic acid from other salts than the ammonium salt of hydroxycarboxylic acid.

In the present invention, the ammonium salt of hydroxycarboxylic acid and phosphate and/or sulfate included in the aqueous solution are converted into hydroxycarboxylic acid and phosphoric acid and/or sulfuric acid, respectively, and then hydroxycarboxylic acid is converted into acrylic acid using the phosphoric acid and/or sulfuric acid as a catalyst. Therefore, acrylic acid can be economically prepared without further addition of catalysts.

Further, since a homogeneous catalyst such as phosphoric acid and/or sulfuric acid is used, it is not necessary to consider the lifetime problem of catalyst associated with use of heterogeneous catalysts, and generation of organic impurities during dehydration can be minimized, thereby minimizing contaminants in a dehydration tube.

Hereinafter, the present invention will be described in detail with reference to Examples as follows. However, the following Examples are for illustrative purposes only, and the invention is not intended to be limited by these Examples.

Example 1

1) Preparation of Aqueous Solution

The glycerol dehydrogenase genes, dhaB123-gdrA and gdrB were amplified from the genomic DNA of *Klebsiella pneumonia* (DSM 2026) by PCR, and inserted into the NcoI-EcoRI and EcoRI-SalI sites, respectively, of the pET-Duet vector (Novagen) to prepare a pET-BAB vector. The primers used for amplification of dhaB123-gdrA gene are as follows.

```
Forward primer (SEQ ID NO. 1):
ATATCATGAAAAGATCAAAACGATTT (BspHI)

Reverse primer (SEQ ID NO. 2):
AAAGAATTCCGCGAGCGCCCGTTTAATTC (EcoRI)
```

The primers used for amplification of gdrB gene are as follows.

```
Forward primer (SEQ ID NO. 3):
TTTGAATTCTAACGAGGGGACCGTCATGTC (EcoRI)

Reverse primer (SEQ ID NO. 4):
TAGTCGACTCAGTTTCTCTCACTTAACGG (SalI)
```

PCR was performed under the conditions of Cycle I (95° C., 5 min), Cycle II (30 cycles/95° C., 30 sec/55° C., 30 sec/72° C., 5 min (dhaB123-gdrA) or 30 sec (gdrB)), Cycle III (72° C., 5 min).

To insert a PCR product of the pseudo-gene amplified from the pET-Duet vector into the prepared pET-BAB vector, a nucleotide sequence (GCTAGC) corresponding to NheI is added downstream of NdeI containing the start codon of pET-BAB vector, so as to prepare a pET-BAB-(NheI) vector. PCR was performed under the conditions of Cycle I (95° C., 5 min), Cycle II (30 cycles/95° C., 30 sec/55° C., 30 sec/72° C., 30 sec), Cycle III (72° C., 5 min). The primers used are as follows:

```
Forward primer (SEQ ID NO. 5):
TTTCATATGGCTAGCGCTCGTCGTTTGGTATGGCTTC
(NdeI & NheI)

Reverse primer (SEQ ID NO. 6):
TTTGGTACCTTTTGCCTTCCTGTTTTTGCTC (KpnI)
```

Genomic DNA was extracted from Cupriavidus necator ATCC 17699, and PCR was performed using a forward primer (SEQ ID NO. 7: AAAGCTAGCATGTACCAGGATCTCGCCC (NheI)) and a reverse primer (SEQ ID NO. 8: AATGGTACCTCAGGCCTGGGTGATGAACTT (KpnI)) to amplify the 3-HPA oxidase gabD4 gene, which was digested with NheI and KpnI. PCR was performed under the conditions of Cycle I (95° C., 5 min), Cycle II (30 cycles/95° C., 30 sec/55° C., 30 sec/72° C., 1 min 45 sec), Cycle III (72° C., 5 min).

The amplified DNA was introduced into the pTrcHisC vector (Invitrogen) treated with the same enzyme so as to prepare a pTH-Cn-gabD4 vector. The pTH-Cn-gabD4 was digested with NheI and KpnI, and then inserted into the prepared pET-BAB-(NheI) vector to prepare a recombinant vector pET-BAB-gabD4. The resulting recombinant vector pET-BAB-gabD4 and pET-BAB-aldH vector were transformed into *E. coli* BL21(DE3) so as to prepare a recombinant strain producing 3-hydroxypropionic acid from glycerol. The recombinant strain thus prepared was pre-cultured in a 500 ml-flask containing 100 ml of LB (Luria Bertani) medium supplemented with 50 µg/ml ampicillin at 37° C., and then cultured in a 5 L-fermentor containing 2 L of medium (12.8 g/L of $Na_2HPO_4\cdot7H_2O$, 3 g/L of $KH_2PO_4$, 1.5 g/L of NaCl, 2 g/L of $NH_4Cl$, 17.4 g/L of $K_2HPO_4$, 0.5 g/L of yeast extract, 120 mL of 1M $MgSO_4$, 4 mL of 1M $CaCl_2$, 80 g/L of Glycerol, pH 7.8) at the same temperature. Then, when OD600 is 0.6~0.8, 0.03mM IPTG and 48 µM vitamin B12 were added to induce protein expression and 3-hydroxypropionic acid production.

After induction of expression, the cells were cultured for 48 hours to produce 32 g/L of 3-hydroxypropionic acid. The content of 3-hydroxypropionic acid was quantified by HPLC (Waters e2695) of 1 ml of the fermentation broth. In HPLC analysis, an Aminex HPX-87H column and 0.5% sulfuric acid containing 9% acetonitrile as a solvent were used. The temperature of the column was 35° C., and the detector was operated in an IR and UV/VIS (210 nm) dual mode. The fermentation broth was centrifuged at 4000 rpm for 15 minutes to remove cell precipitates, and the supernatant was obtained.

2) Formation of Conversion Aqueous Solution

The supernatant of the fermentation broth thus obtained was contacted with (passed through) the cation exchange resin Trilite CMP28 (1 kg, Samyang, porous type of a copolymer of styrene and DVB (Divinyl benzene), exchange group: sulfonic acid group) packed in the column (packing amount: 1 L) to remove ammonium ions and metal ions, and thus an aqueous solution containing 3-hydroxypropionic acid, phosphoric acid and sulfuric acid was obtained. The column was washed with water, and water was removed from an eluent containing the obtained aqueous solution and the washing solution using a vacuum dewatering system at 50° C. and 100 torr, so as to form a conversion aqueous solution containing 10 wt % of 3-hydroxypropionic acid (3-HP), phosphoric acid and sulfuric acid.

3) Dehydration (Preparation of Acrylic Acid)

A stainless reactor having an inner diameter of 10 mm and a height of 100 mm was packed with glass beads having a diameter of 1.5 mm at a height of 50 mm as a packed bed. The temperature inside the reactor was heated to 190° C., and the conversion aqueous solution obtained in step 2 was supplied to the upper part of the reactor at a flow rate of 0.25 ml/min. A nitrogen gas was also injected at a flow rate of 100 ml/min at the same time. The vaporized water and products in the reactor were discharged, and cooled, and then a trapping solution was recovered.

Comparative Example 1

A 3-hydroxypropionic acid (ca. 30% in Water, Tokyo Chemical Industry) reagent was dissolved in water to prepare 10 wt % of an aqueous solution. A stainless reaction tube having an inner diameter of 10 mm was packed with glass beads having a diameter of 1.5 mm at a height of 200 mm as a packed bed for diffusion of raw materials and heat transfer. The temperature outside the reaction tube was heated to 350° C., and the raw material composition was supplied to the upper part of the reaction tube at a flow rate of 0.25 ml/min. A nitrogen gas was also injected at a flow rate of 100 ml/min at the same time. The reaction gas in the bottom of the reaction tube was discharged, and cooled, and then a trapping solution was recovered.

Comparative Example 2

A trapping solution was recovered in the same manner as in Example 1, except that the aqueous solution containing 3-hydroxypropionic acid ammonium, phosphate and sulfate prepared in Example 1 was contacted with the cation exchange resin of Example.

Experimental Example

The trapping solutions of Example 1 and Comparative Examples 1 and 2 were analyzed by high performance liquid chromatography under the following conditions, and the results were applied to the following Equations 1 and 2 to determine the conversion rate of 3-hydroxypropionic acid and selectivity of acrylic acid. The results measured are shown in the following Table 1.

Analysis Conditions of High Performance Liquid Chromatography
  Column used: ACQUITY UPLC®BEH C18
  Injection volume of sample: 1 ml
  Flow rate of mobile phase solution: 0.200 ml/min
  Mobile phase solution: 0.1 mol phosphoric acid aqueous solution
  Absolute calibration
  Detection: UV 210 nm Conversion rate (%) of 3-hydroxypropionic acid (3-HP)=concentration (%, w/w) of 3-hydroxypropionic acid before dehydration−concentration (%, w/w) of 3-hydroxypropionic acid after dehydration/concentration (%, w/w) of 3-hydroxypropionic acid before dehydration  [Equation 1]

Selectivity (mol %) of acrylic acid=concentration (%, w/w) of acrylic acid after dehydration×90/(concentration (%, w/w) of 3-hydroxypropionic acid before dehydration−concentration (%, w/w) of 3-hydroxypropionic acid after dehydration)×72  [Equation 2]

TABLE 1

|  | 3-HP conversion rate (%) | Acrylic acid selectivity (mol %) |
|---|---|---|
| Example 1 | 95% | 98 mol % |
| Comparative Example 1 | 75% | 98 mol % |
| Comparative Example 2 | 80% | 80 mol % |

As shown in Table 1, when the catalyst was not used during dehydration in Comparative Example 1, the conversion rate of 3-hydroxypropionic acid was decreased and, thus, productivity of acrylic acid (conversion rate of 3-HP×selectivity of acrylic acid) was decreased as compared to Example 1 of the present invention using the catalyst obtained from the salt of inorganic acid.

Further, when the ammonium salt of 3-hydroxypropionic acid was used without conversion into 3-hydroxypropionic acid (no use of cation exchange resin) in Comparative Example 2, the conversion rate of 3-hydroxypropionic acid and selectivity of acrylic acid were decreased as compared to Example 1 of the present invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for preparing an unsaturated carboxylic acid, comprising the steps of:
   (a) providing an aqueous solution comprising an ammonium salt of a hydroxycarboxylic acid and a salt of an inorganic acid;
   (b) contacting the aqueous solution with a cation exchange resin to prepare a conversion aqueous solution comprising the hydroxycarboxylic acid and the inorganic acid, wherein the cation exchange resin has an acid dissociation constant (pKa) lower than a pKa of the inorganic acid, and the concentration of the inorganic acid in the conversion aqueous solution is 0.1 to 5 wt %, based on the conversion aqueous solution; and
   (c) dehydrating the hydroxycarboxylic acid in the conversion aqueous solution comprising the hydroxycarboxylic acid and the inorganic acid using the inorganic acid comprised in the conversion aqueous solution as a catalyst.

2. The method according to claim 1, wherein the salt of inorganic acid comprises one or more selected from the group consisting of phosphate and sulfate of inorganic acid.

3. The method according to claim 1, wherein the aqueous solution comprising the ammonium salt of hydroxycarboxylic acid and the salt of inorganic acid is a fermentation broth of a microorganism, or a aqueous component thereof.

4. The method according to claim 1, wherein the cation exchange resin has an acid dissociation constant (pKa) of 0.5 less than a pKa of the inorganic acid.

5. The method according to claim 1, wherein the hydroxycarboxylic is one or more selected from the group consisting of lactic acid, citric acid, malic acid, tartaric acid, glycolic acid, 3-hydroxypropionic acid, 3-hydroxy-2-methylpropionic acid, 3-hydroxybutyric acid, 3-hydroxyvaleric acid, 3-hydroxyhexanoic acid, 3-hydroxyheptanoic acid, 3-hydroxyoctanoic acid, 3-hydroxy-2-methylbutyric acid, 3-hydroxy-2-methylpentanoic acid, 3-hydroxy-3-methylbutyric acid, 2,3-dimethyl-3-hydroxybutyric acid and 3-hydroxy-3-phenylpropionic acid.

6. The method according to claim 1, wherein the contacting step further comprises regenerating ammonia by washing the ammonium ion adsorbed to cation exchange resin with an acid.

7. The method according to claim 1, wherein the content of the ammonium salt of hydroxycarboxylic acid in the aqueous solution is 0.1 to 50 w/v %, based on 100 w/v % of the aqueous solution.

8. The method according to claim 1, wherein the content of hydroxycarboxylic acid in the conversion aqueous solution is 5 to 95 wt %, based on 100 wt % of the conversion aqueous solution.

9. The method of claim 1, wherein dehydrating the hydroxycarboxylic acid comprises adding a water miscible solvent to the conversion aqueous solution and subsequently heating the conversion aqueous solution and the water miscible solvent.

10. The method of claim 1, wherein dehydrating the hydroxycarboxylic acid comprises heating the conversion aqueous solution.

\* \* \* \* \*

SEQUENCE LISTING

<160> NUMBER OF SEQ ID NOS: 8

<210> SEQ ID NO 1
<211> LENGTH: 26
<212> TYPE: DNA
<213> ORGANISM: Artificial Sequence
<220> FEATURE:
<223> OTHER INFORMATION: Synthetic (Forward primer used for
      amplification of dhaB123-gdrA gene)

<400> SEQUENCE: 1
atatcatgaa aagatcaaaa cgattt                                          26

<210> SEQ ID NO 2
<211> LENGTH: 29
<212> TYPE: DNA
<213> ORGANISM: Artificial Sequence
<220> FEATURE:
<223> OTHER INFORMATION: Synthetic (Reverse primer for amplification of
      dhaB123-gdrA gene)

<400> SEQUENCE: 2
aaagaattcc gcgagcgccc gtttaattc                                  29

<210> SEQ ID NO 3
<211> LENGTH: 30
<212> TYPE: DNA
<213> ORGANISM: Artificial Sequence
<220> FEATURE:
<223> OTHER INFORMATION: Synthetic (Forward primer for amplification of
      gdrB gene)

<400> SEQUENCE: 3
tttgaattct aacgagggga ccgtcatgtc                                 30

<210> SEQ ID NO 4
<211> LENGTH: 29
<212> TYPE: DNA
<213> ORGANISM: Artificial Sequence
<220> FEATURE:
<223> OTHER INFORMATION: Synthetic (Reverse primer for amplification of
      gdrB gene)

<400> SEQUENCE: 4
tagtcgactc agtttctctc acttaacgg                                  29

<210> SEQ ID NO 5
<211> LENGTH: 37
<212> TYPE: DNA
<213> ORGANISM: Artificial Sequence
<220> FEATURE:
<223> OTHER INFORMATION: Synthetic (Forward primer)

<400> SEQUENCE: 5
tttcatatgg ctagcgctcg tcgtttggta tggcttc                         37

<210> SEQ ID NO 6
<211> LENGTH: 31
<212> TYPE: DNA
<213> ORGANISM: Artificial Sequence
<220> FEATURE:
<223> OTHER INFORMATION: Synthetic (Reverse primer)

<400> SEQUENCE: 6
tttggtacct tttgccttcc tgtttttgct c                               31

<210> SEQ ID NO 7
<211> LENGTH: 28
<212> TYPE: DNA
<213> ORGANISM: Artificial Sequence
<220> FEATURE:
<223> OTHER INFORMATION: Synthetic (Forward primer for amplifying the
      3-HPA oxidase gabD4 gene)

<400> SEQUENCE: 7
aaagctagca tgtaccagga tctcgccc                                   28

<210> SEQ ID NO 8

```
<211> LENGTH: 30
<212> TYPE: DNA
<213> ORGANISM: Artificial Sequence
<220> FEATURE:
<223> OTHER INFORMATION: Synthetic (Reverse primer for amplifying the
      3-HPA oxidase gabD4 gene)

<400> SEQUENCE: 8
aatggtacct caggcctggg tgatgaactt                                        30
```